United States Patent [19]
Hulings et al.

[11] Patent Number: 6,065,154
[45] Date of Patent: May 23, 2000

[54] SUPPORT GARMENTS FOR PATIENT-WORN ENERGY DELIVERY APPARATUS

[75] Inventors: Robert J. Hulings, Mars; Emil Oskin, Natrona Heights; Arlan J. Brandt, Gibsonia, all of Pa.

[73] Assignee: Lifecor, Inc., Pittsburgh, Pa.

[21] Appl. No.: 09/056,315

[22] Filed: Apr. 7, 1998

[51] Int. Cl.[7] .......................... A41D 1/04; A61B 5/0402
[52] U.S. Cl. .................... 2/102; 2/94; 2/247; 600/389; 600/393
[58] Field of Search .................... 2/102, 94, 338, 2/913, 919, 920, 247, 250, 114, 400, 83, 69; 600/382, 386, 388, 389, 390, 393

[56] References Cited

U.S. PATENT DOCUMENTS

| | | | |
|---|---|---|---|
| 2,688,752 | 9/1954 | Sbarra et al. ............................... | 2/247 |
| 3,409,007 | 11/1968 | Fuller ......................................... | 2/102 |
| 3,664,560 | 5/1972 | Perkins ....................................... | 2/338 |
| 3,897,785 | 8/1975 | Barto, Jr. ................................. | 128/295 |
| 4,580,572 | 4/1986 | Granek et al. . | |
| 4,583,547 | 4/1986 | Granek et al. . | |
| 4,608,987 | 9/1986 | Mills ....................................... | 128/639 |
| 4,698,848 | 10/1998 | Buckley ...................................... | 2/250 |
| 4,729,377 | 3/1988 | Granek et al. . | |
| 4,889,131 | 12/1989 | Salem et al. . | |
| 5,007,427 | 4/1991 | Suzuki et al. .............................. | 2/102 |
| 5,224,479 | 7/1993 | Sekine ...................................... | 128/644 |
| 5,361,412 | 11/1994 | Perry ........................................... | 2/247 |
| 5,413,262 | 5/1995 | Dewire et al. ............................. | 2/338 |
| 5,611,085 | 3/1997 | Rasmussen .................................. | 2/94 |
| 5,708,978 | 1/1998 | Johnsrud .................................... | 2/102 |
| 5,758,366 | 6/1998 | Wilson ....................................... | 2/338 |

*Primary Examiner*—Amy B. Vanatta
*Attorney, Agent, or Firm*—Buchanan Ingersoll, P.C.

[57] ABSTRACT

In a support garment for a patient-worn energy delivery apparatus, a vest-type garment holds an electrode belt in contact with a wearer's ribcage. The garment includes a flap with button holes to permit buttoning in of energy transfer electrodes, thus constituting a wearable electrode system. Additionally, a holster contains the components of a wearable cardioverter defibrillator that are not in contact with the skin. The holster has an adjustment for waist, girth and vertical position of the defibrillator according to the personal preferences of the wearer. The support garment includes a vest-like chest garment and an inner layer which provides support for the defibrillator electrodes. A removable electrode harness is attachable to the support garment in order to accurately position the sensing electrodes on the body of the wearer and energy delivery electrodes for transfer of an electrode therapy pulse to the wearer of the garment. The chest garment includes adjustable shoulder straps and waist belt so that the support garment can accommodate any body size or shape.

15 Claims, 10 Drawing Sheets

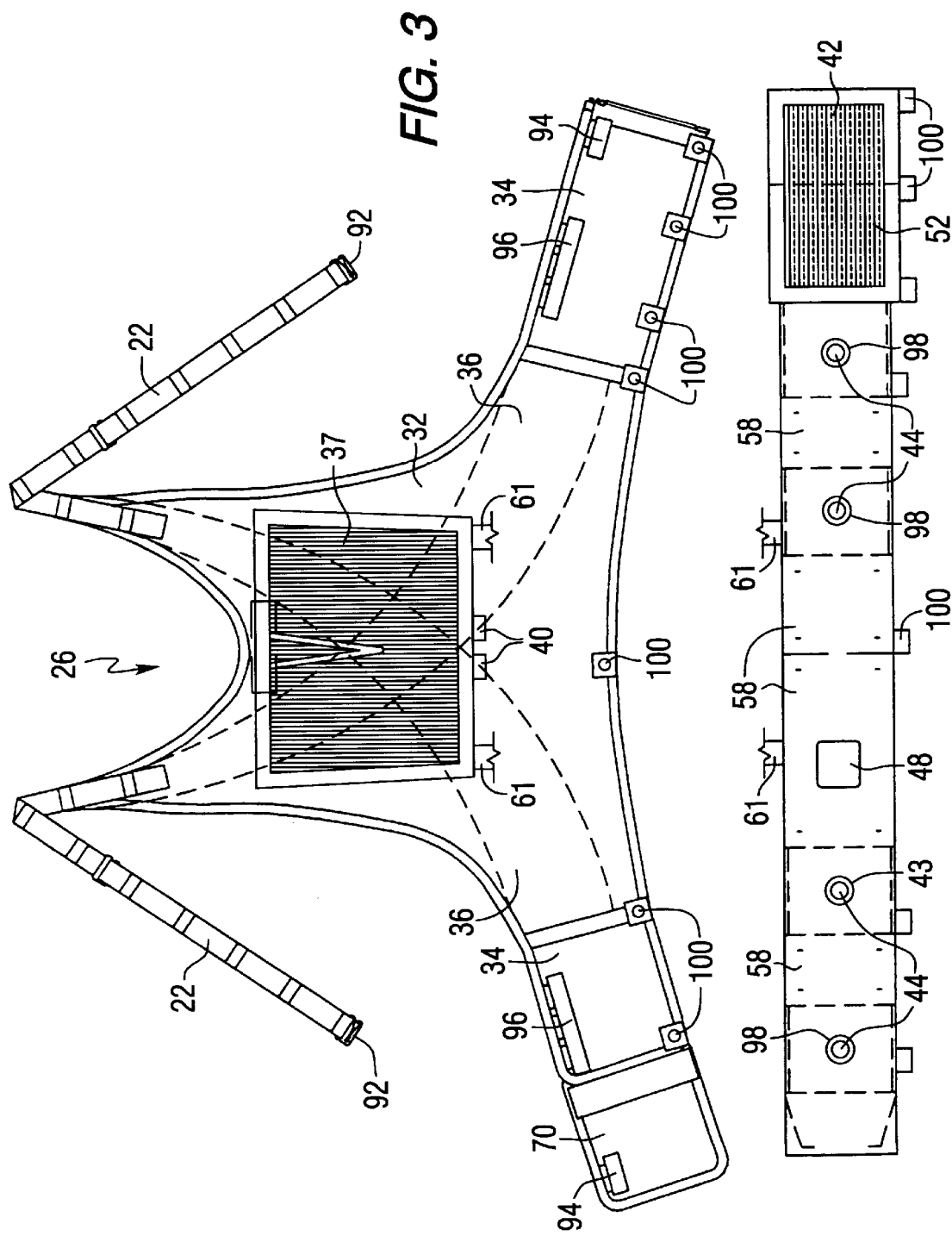

SUPPORT GARMENTS FOR PATIENT-WORN ENERGY DELIVERY APPARATUS

BACKGROUND OF THE INVENTION

1. Field of the Invention

This invention relates generally to a wearable cardioverter-defibrillator device and more particularly to support garments for housing the device and its associated sensing and energy delivery electrodes.

2. Description of the Related Art

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each may lead to death within minutes unless corrected by the appropriate electrical stimulation.

One of the most deadly forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment may result in death, implantable pacemakers and defibrillators have significantly improved the ability to treat these otherwise life threatening conditions. Being implanted within the patient, the device continuously monitors the patient's heart for treatable arrhythmias and when such is detected, the device applies corrective electrical pulses directly to the heart.

Normal heart function often can be restored to a person suffering ventricular fibrillation or ventricular tachycardia by a procedure known as cardioversion, the synchronized application of electric therapy to the heart muscle. Pacemakers and defibrillators that apply corrective electrical pulses externally to the patient's chest wall also are used to correct such life-threatening arrhythmias but suffer from a drawback insofar as it may not be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. Alternatively, such patients are kept in a hospital where corrective electrical therapy is generally close at hand. Long term hospitalization, however, is frequently impractical due to its high cost, or due to the need for patients to engage in normal daily activities.

There also are many patients susceptible to heart arrhythmias who are at temporary risk of sudden death. For example, patients who have suffered a myocardial infarction are at substantial risk of tachyarrhythmias for several weeks thereafter. Such patients generally are hospitalized but could be discharged earlier if there were a practical means to protect them from life threatening arrhythmias. Additionally, patients awaiting implantation of an automatic defibrillator may require an external defibrillator to be close at hand, in case they experience a life-threatening tachyarrhythmia. Furthermore, some patients who may benefit from an implantable defibrillator may face an inordinate risk from the surgery required for implanting such a device.

A wearable external defibrillator is disclosed in U.S. patent application Ser. No. 08/651,274, filed on May 23, 1996 and assigned to the assignee hereof, which application is incorporated herein by reference. The wearable defibrillator provides a patient-worn energy delivery apparatus for imparting electrical therapy to the body of a patient responsive to detection of a treatable condition. An important consideration in the proper operation of the device is accurate sensing of the treatable condition by the apparatus and delivery of the electrical energy to the person's body by electrodes. The electrodes must be placed on the person's body in the correct position in order to effectively perform these functions. It is desirable that the electrodes be positioned on both the front and back of the patient in order to provide the most effective electrical therapeutic pulse to the body. Additionally, since the wearable defibrillator is designed to be worn by the patient over extended periods of time, the use of skin-irritating substances commonly used on a more temporary basis to attach electrodes to a patient should be eliminated.

What is needed then is an apparatus for supporting the device while accurately positioning the wearable defibrillator electrodes on a patient's body, even during typical body motion, and most especially those occurring when the patient is experiencing an arrhythmic episode.

SUMMARY OF THE INVENTION

The present invention provides support garments for a patient-worn energy delivery apparatus for holding the defibrillator device and its associated sensing and energy delivery electrodes. The garment includes a vest-like chest garment and an inner layer which provides support for the defibrillator electrodes. A removable electrode harness is attachable to the support garment in order to accurately position sensing electrodes and energy delivery electrodes on a patient's body.

The chest garment includes adjustable shoulder straps and an adjustable waist belt so the support garment can accommodate any body size or shape.

The wearable cardioverter-defibrillator support garments provide comfort and functionality under circumstances of human body dynamics, such as bending, twisting, rotation of the upper thorax, semi-reclining and lying down. These are positions that a patient would assume if they were to become unconscious due to an arrhythmic episode. The design of the chest garment is such that it minimizes bulk, weight and undesired concentrations of force or pressure, while providing the necessary radial forces upon the sensing and energy delivery electrodes to ensure device functionality. The sensing electrodes are distributed around the circumference of the chest garment and are held against the patient's skin by these forces. Also held by these forces are three energy delivery electrodes, one located at the patient's left front and two located at the center of the patient's back.

BRIEF DESCRIPTION OF THE DRAWINGS

FIG. 3 is an exploded view of the inside of the support garment of the present invention showing an inner layer separated from the chest garment.

DETAILED DESCRIPTION OF THE PREFERRED EMBODIMENTS

Figure 1:
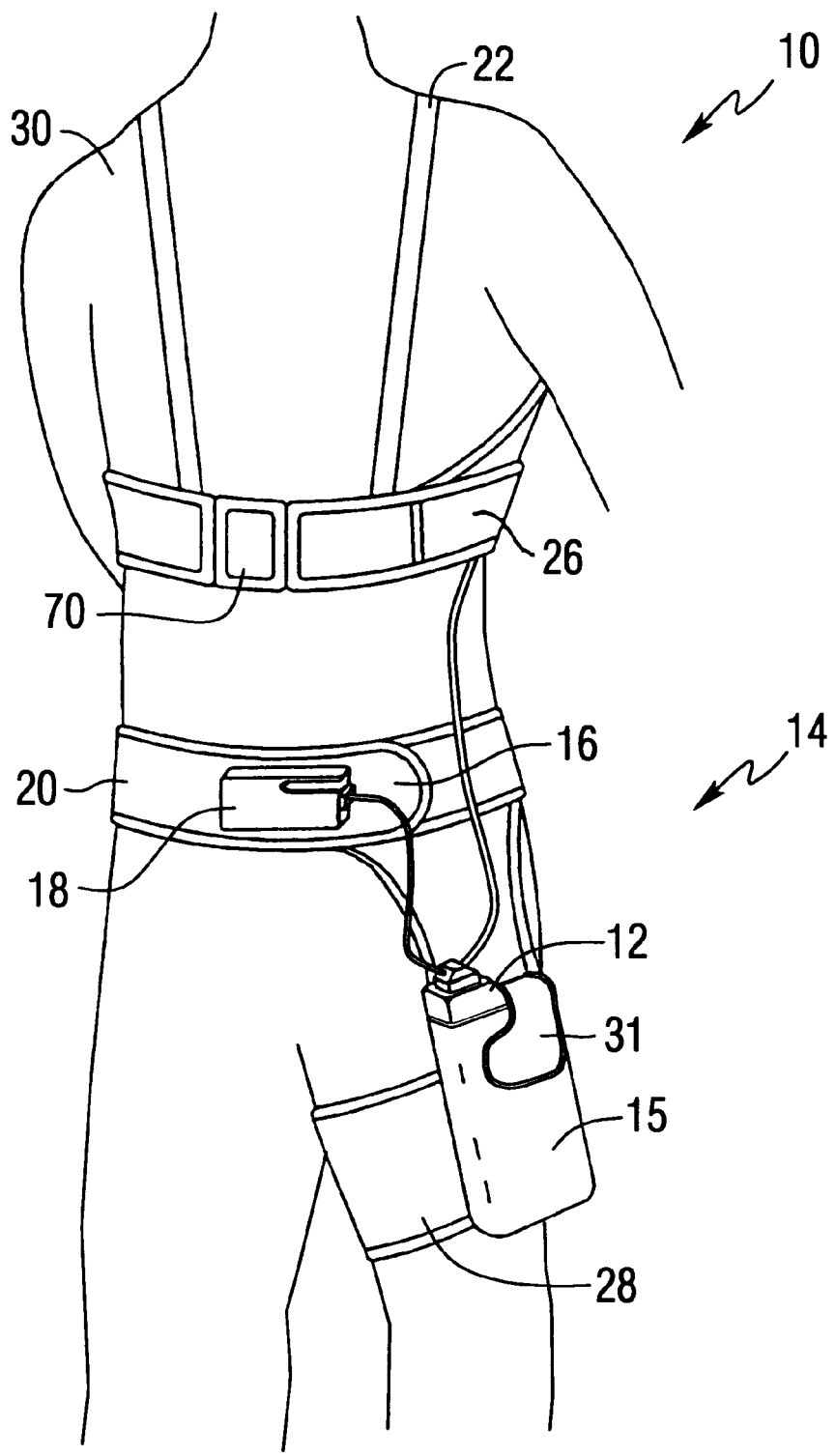
FIG. 1 is an illustration of a patient-worn energy delivery apparatus utilizing support garments of the present invention.
Figure 2:
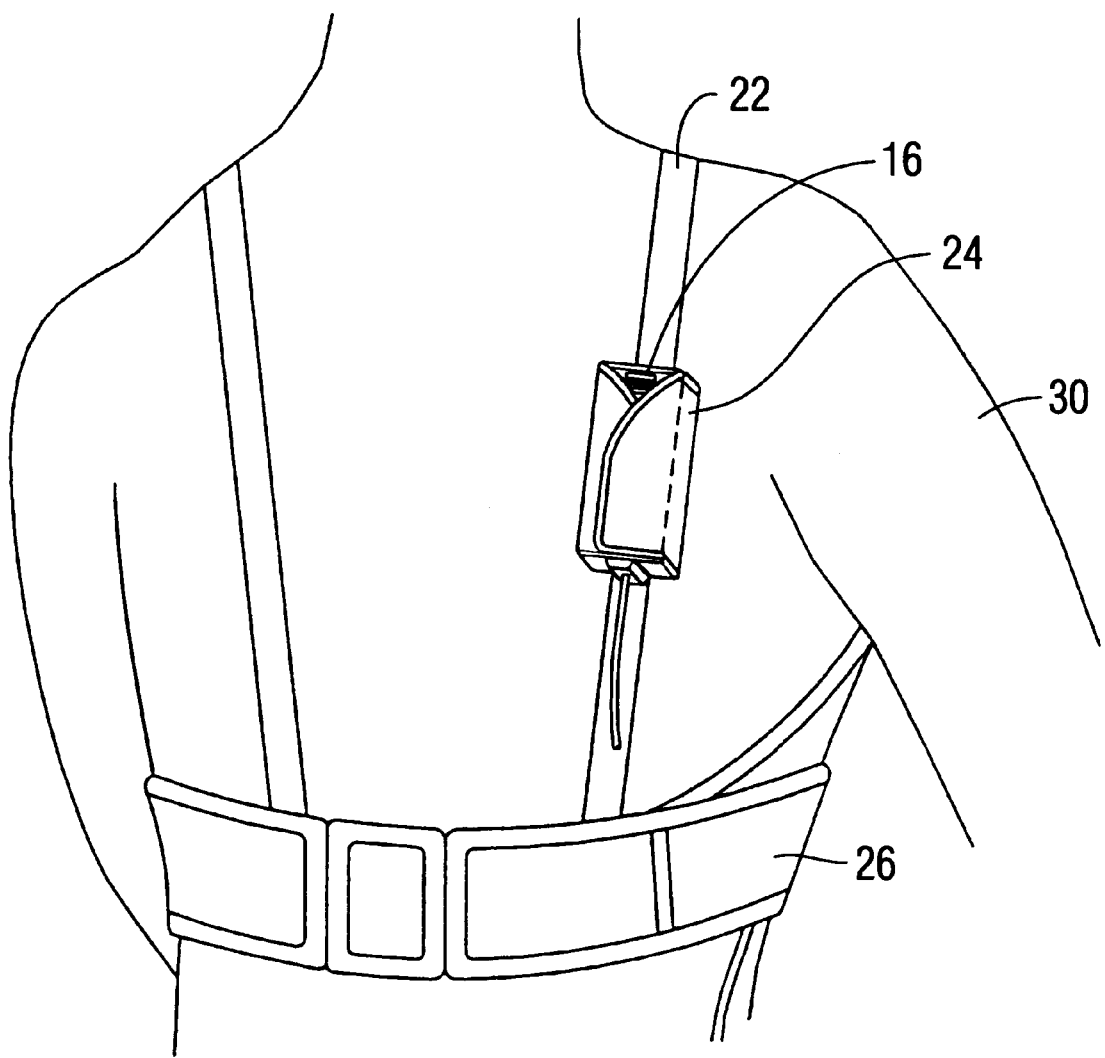
FIG. 2 is an illustration of an alternate patient display location attached to a chest garment strap of the present invention for use of the wearable defibrillator during sleep.

Referring now to the drawings in detail, FIG. 1 shows support garments 10 for a patient-worn energy delivery apparatus which includes a monitor-defibrillator 12 disposed in a support holster 14. Also included is a display unit 16 that the patient uses to interact with the monitor-defibrillator 12. The display 16 is preferably normally carried in a pouch 18 attachable to a waist belt 20 incorporating the holster 14. The attachment is preferably made by means of fabric hook and pile fasteners (not shown). The entire outer surface of the holster 14 and the belt 20 are of a nylon pile, permitting the patient to attach the display wherever is convenient. In an alternative embodiment (FIG. 2), a pouch 24 may be attached to a shoulder strap 22 of a chest garment 26 of the support garment 10. This is the preferred position, for example, during sleep. If desired, a thigh strap 28 may be utilized to restrain the lower end of the monitor holster 14 as will be described in more detail hereinafter. During wear, it is desired that the display unit 16 be accessible at all times to the patient 30. The holster includes a pocket 15 for retaining the monitor-defibrillator 12. The monitor-defibrillator is held in the pocket 15 by flap 31.

Figure 4A:
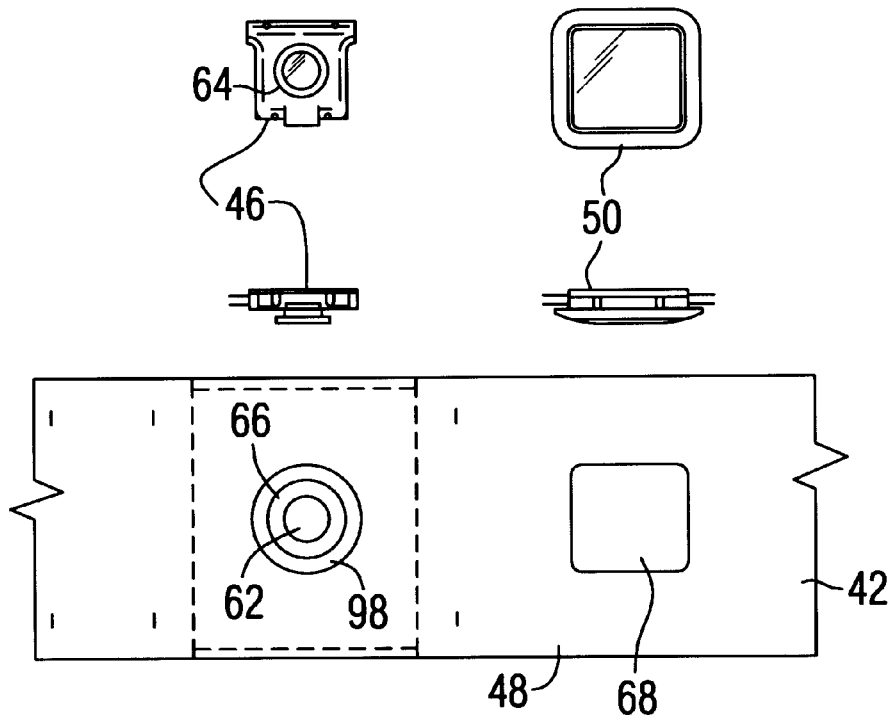
FIG. 4 is a side view of the inner layer shown in FIG. 3.
Figure 4B:
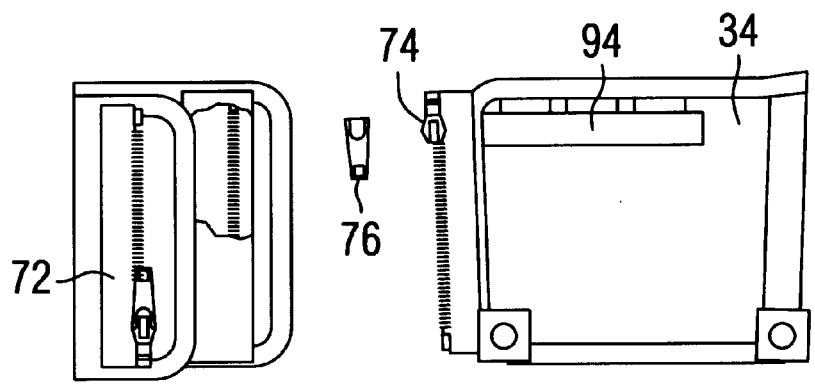
Figure 5:
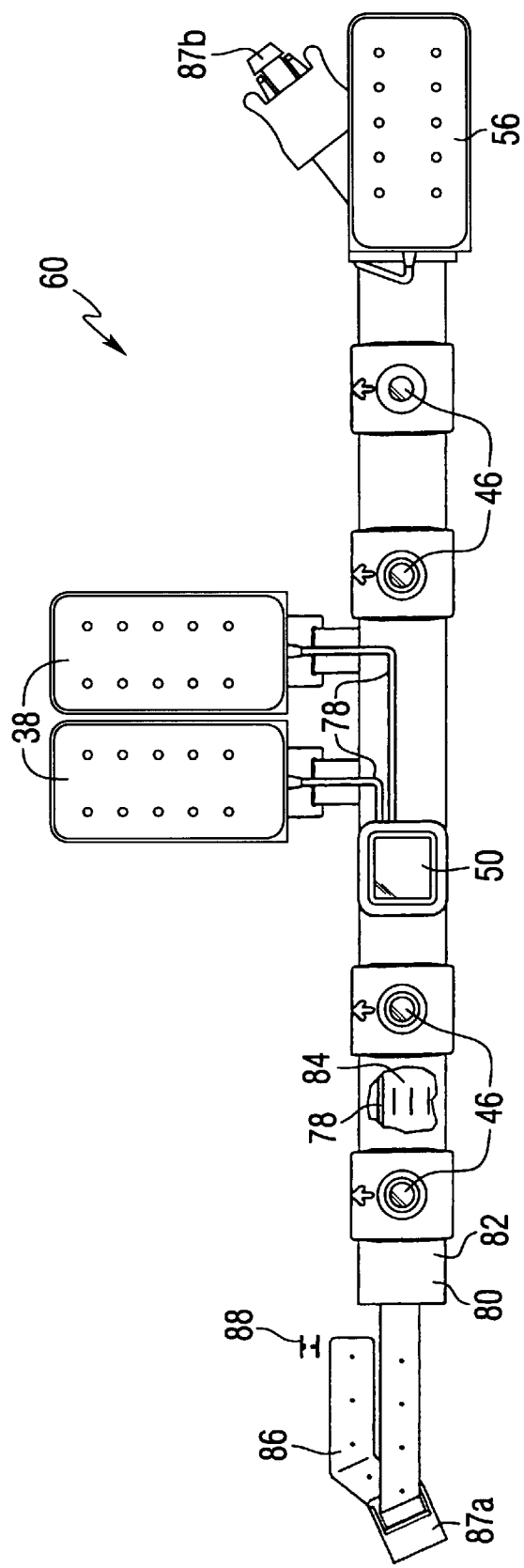
FIG. 5 is a detailed view of an electrode harness for the support garment of the present invention.

Referring now to FIGS. 3–5, the support garments 10 of the present invention comprise the chest garment 26 having a back panel 32, side portions 34, and back reinforcements 36. These side portions extend laterally from either side of the lower portion of the chest garment, and are attachable to each other to define a waist for the chest garment 26. Preferably, the chest garment 26 is made of open-weave elasticized mesh fabric with unequal bi-directional stretch. The fabric is oriented in the case of the back panel 32 and side portion extensions 34 so that the most aggressive stretch axis is placed horizontally with respect to the support garment 10 (and hence the patient 30). This ensures that maximum available inward force is applied to the electrode axis during wear, to enhance electrode function while minimizing fabric coverage on the patient's body, thereby enhancing comfort. In the case of the back reinforcements 36, the fabric is oriented so that the most aggressive stretch axis is located diagonally to the chest garment 26, or along the long axis of the reinforcement, to optimize forces upon the rear energy delivery electrodes which are placed in pocket 37, attached to the inside surface of the chest garment back panel 32 and used to retain two rear energy delivery electrodes 38 (FIG. 5). In a preferred embodiment, the pocket 37 is made from a non-elastic mesh fabric designed to isolate the metallic energy delivery electrode 38 surfaces from the skin of the patient while allowing a conductive gel (not shown) that is automatically extruded from the electrodes to easily pass through. This gel is extruded from capsules within the electrode housings upon receipt of a signal from the monitor-defibrillator 12 after declaration by the detection circuitry within the monitor-defibrillator of the occurrence of a treatable cardiac condition. The forces applied to the electrodes by the fabric, in addition to the use of the conductive gel, helps ensure that proper contact and electrical conductivity with the patient's body are maintained, even during body motions. Conventional snap fasteners 40 close the pocket 37 once the electrodes 38 are inserted. These components are also referred to as the chest garment outer shell.

Attached to the chest garment 26 but shown separated in FIG. 3 for clarity is a layer 42. This inner layer is preferably assembled from a soft, body-contacting fabric, and most preferably a Coolmax-Lycra blend. Zones 44 are provided in the inner layer 42 for placement of sensing electrodes 46 (FIG. 5). An additional zone 48 is provided for a driven ground electrode 50 and a second pocket 52, constructed in a manner similar to that as is the rear energy delivery electrode pocket 37, is provided for a front energy delivery electrode 56. As shown in detail in FIG. 3, segments 58 of open cell elastomeric foam are provided between all of the electrode zones 44 and 48 to provide padding and a uniform circumference to the support garment 10 when the electrode harness 60 (FIG. 5) that releasably fastens to the inner layer 42 is inserted. These foam segments 58 are preferably enclosed by the Coolmax-Lycra fabric of the inner layer 42. The upper section of the inner layer 42 is preferably permanently attached to the chest garment 26 by straps 61, which are shown broken for clarity.

Referring to the inner layer 42 detail shown in FIG. 4a, preferably sewn in the center of sensing electrode zones 44 are holes or ports 62 in the Coolmax-Lycra fabric for the sensing electrode button heads 64 to "snap" into. These holes or ports include elastomeric O-rings 66 sandwiched between the Coolmax-Lycra layers that form the inner layer imparting shape to the port 62, and providing a retaining member surrounding the sensing electrode button heads 64. The driven ground electrode 50 has a like port 68 sewn into the inner layer fabric to retain the ground electrode. This port may or may not have an O-ring fitted therein. In this way, the electrodes 46, 50 are removably attachable to the ports 62, 68, which allows the electrode harness 60 to be removably attached to the inner layer 42 of the chest garment 26.

Preferably, six basic garment sizes are provided, proportioned to fit patients 30 from twenty-five (25) inches chest circumference to fifty-five (55) inches chest circumference. The various sizes are dimensioned so that the proper electrode spacing is implemented and maintained. The inter-zone distance, which is the distance between the sensing electrodes, each other and the driven ground electrode, is proportional to the circumference the garment is to fit. The garment is constructed using tolerances that are considerably closer than those customarily used in the garment trades. The materials of construction are chosen for functionality, comfort and biocompatibility. The materials wick perspiration from the skin.

Unequal omnidirectional and bi-directional stretch of the fabrics has been implemented to apply the necessary forces onto the various electrodes in the harness, while the patient is in various body positions or during motions resulting from normal daily activities. These means allow the use of capacitive or other non-ionic sensing electrodes thereby enhancing patient comfort and adding significant noise immunity. These electrode types avoid the necessity of using adhesively attached electrodes, such as those used for short term monitoring during Holter studies or monitoring in an intensive care facility. Also avoided are electrodes requiring conductive gel or other skin preparing substances. As the patient-worn energy delivery device is designed to be used by the patient for relatively long-term monitoring (up to six months), the non-adhesive and non-ionic electrodes provide comfort and long life and precludes the patient having to change electrodes after a short wear time.

Precise fitting, within a garment size, is accomplished by means of an end section 70, shown extended and attached to the garment outer shell in FIG. 3, and separated and shown folded over for clarity in FIG. 4b at item 72. These end sections are preferably provided in one inch increments to the fitter for fine adjustment to the chest circumference. The sections are attached to the chest garment 26 with a locking slide fastener 74. The slide fastener tab 76 is removed once the appropriate end section length is determined and installed. This precludes further adjustment by the patient. In the event of a patient having a significant weight gain or loss, the fitter, at the patient's periodic checkup, is able to replace the end section with one sized more appropriately to the patient's current measurements.

Referring in detail to FIG. 5, the electrode harness 60 contains a plurality of sensing electrodes 46, the driven ground electrode 50, the two rear energy delivery electrodes 38 and the front energy delivery electrode 56. The harness 60 also contains a plurality of wiring conductors 78 interconnecting the various electrodes to each other and to the monitor-defibrillator 12. These conductors 78 are enclosed by the flat, tubular fabric structure of the harness cover 80. This structure is assembled with a layer of Coolmax-Lycra fabric 82 facing the patient's body and a layer of wide elasticized fabric 84 on the side away from the body. This elasticized fabric 84 is most preferably chosen to have a low spring rate (low force per inch), to provide sufficient force to the electrode-body interface, over the longest practicable length within a given garment size. The length of this elasticized fabric 84 may be varied, during manufacture, to impart the desired forces applied to the electrodes. The electrode harness cover 80 is fitted with a fabric or elasticized fabric end section 86 and buckle 87 (shown at either end as a female portion 87a and a male portion 87b) that may be adjusted by the fitter for optimum electrode placement and force. Once the belt length is determined, the end section is staked in place with a medical rivet 88, which is non-reversible without destruction. This also precludes further adjustment by the patient, or other inadvertent length changes which could affect performance of the wearable cardioverter-defibrillator.

Preferably, the adjustable length shoulder straps 22 are provided to allow compensation for varying torso lengths and to permit placement of the sensing electrode axis within the desired zone. The straps also contribute to proper placement of the rear energy delivery electrodes 38 and ensure that sufficient pressure is applied to the electrodes in the event of the need to deliver a defibrillation shock upon detection of a treatable arrhythmia. The lower ends 92 (FIG. 3) of the straps 26 may be fastened to the end sections 34 near the center of the chest garment 26, at the sternum, or alternately they may be fastened further out toward the sides, as the patient desires. Termination zones 94 and 96 respectively are provided at these locations. In this way, the support garments can accommodate various body shapes and sizes, as well as both male and female patients. For example, a woman having smaller breasts may be more comfortable wearing the straps at the center (i.e., fastened at termination zones 94), while a woman having more breast tissue may be more comfortable wearing the straps outwards toward the sides (i.e., fastened at termination zone 96). In either case, in an alternative embodiment, the straps 26 may be permanently attached to the garment outer shell in a fixed position, preferably at the side location, since tests have shown this to be an advantageous position for many body types of both sexes.

In a preferred embodiment of the invention, the areas surrounding the sensing electrode zones 44 may be covered or coated with a high-friction elastomer 98 which surrounds the electrode housings, to preclude movement relative to the skin, thus reducing or eliminating motion artifacts on the sensed signals obtained. In addition, capacitive or other non-ionic electrode means are used to further reduce motion artifacts. Further, the system software analyzes the signals obtained from the patient's skin, to detect excessive noise. A low amplitude ac signal is induced onto the patient's skin at the driven ground electrode 50 site. This signal is sensed by each sensing electrodes 46 real-time. If the induced signal becomes erratic or nonexistent, the monitor-defibrillator 12 will alert the patient via a tactile vibrator (not shown) contained within the driven ground electrode housing and an audible message emitted by a speaker in the patient display 16, that the sensing electrode contact within the skin is substandard and that the chest garment 26 needs to be repositioned or adjusted.

The chest garment 26 is constructed to allow the patient to easily disassemble the electrode harness 60 so it may be placed readily into a clean garment. The patient has only to deal with two subassemblies; the chest garment 26 and the electrode harness 60. Disassembly involves releasing the conventional garment snap fasteners 100 that retain the lower section of the garment inner layer 42 to the lower portion of the chest garment and "unbuttoning" the four sensing electrodes 46 and the driven ground electrode 50 from the garment body. The energy delivery electrodes 38, 56 are removed from the chest garment 26 by unfastening conventional garment snaps 40 and removing the electrodes from their pockets 37 and 52. The electrode harness 60 can then be removed from its position between the inner layer and the chest garment outer shell. Complex or unconventional mechanisms are thus avoided, and the patient may be trained rapidly in the assembly and use of the device.

Assembly is the reverse of disassembly. The electrode harness 60 is placed into position between the chest garment 26 and the inner layer 42. The energy delivery electrodes 38, 56 are inserted into their respective pockets 37, 52 and snaps 40 are fastened. The sensing electrodes 46 and the driven ground electrode 50 are "buttoned" into their respective ports 62, 68 in the garment inner layer 42. The inner layer snap fasteners 100 are then closed to hold the electrode harness in place, and thereby provide a wearable external cardio-defibrillator device for a patient 30.

Figure 6:
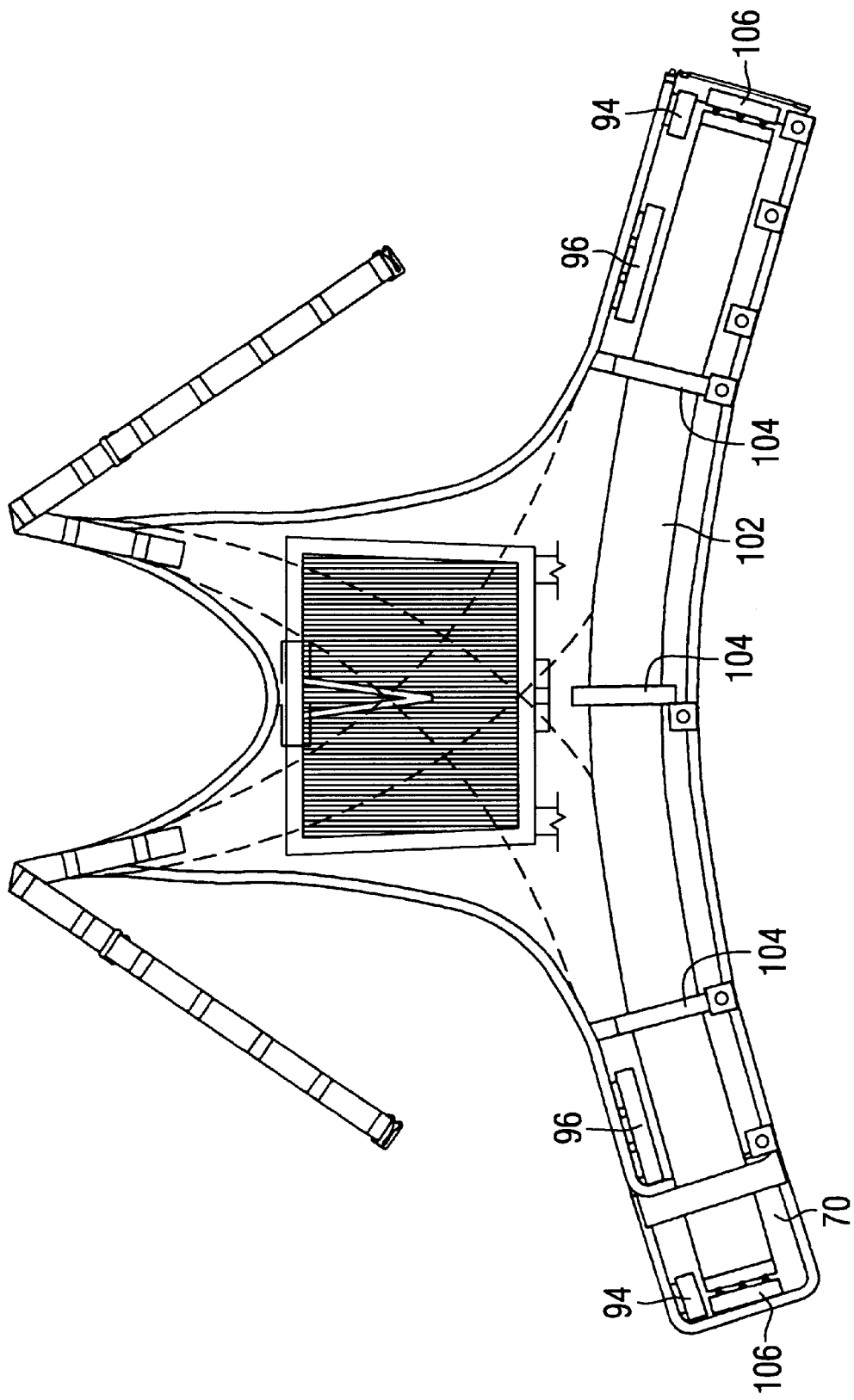
FIG. 6 is an inside view of an alternate embodiment of a chest garment having an elasticized fabric force member attached to a garment outer shell with fabric loops.

FIG. 6 illustrates a preferred embodiment chest garment with an elasticized fabric force member 102 attached to the inside of the garment outer shell with fabric loops 104. Conventional garment trades hook and eye fasteners 106 attach this member to the ends of the garment outer shell. As in a previous embodiment, this member may be varied in length at manufacture to impart the desired forces to the electrodes.

Monitor-Defibrillator holster:

Referring in detail to FIG. 7, the monitor-defibrillator holster 14 comprising the waist belt 20, pocket 15 and thigh strap 28, is constructed from a commercially available comfortable padded fabric manufactured by Velcro USA. It is known in the trade as Trilaminate. This material is a three layer laminate. An inner, skin contacting layer is tricot for comfort. A center layer is elastomeric foam for padding and shape. An outer layer is Nylon pile giving good tensile strength and color and by utilizing fabric hook fasteners, the entire outer layer may be used as the loop or pile portion of the fastener pair, allowing one-size-fits-all adjustment.

Figure 7A:
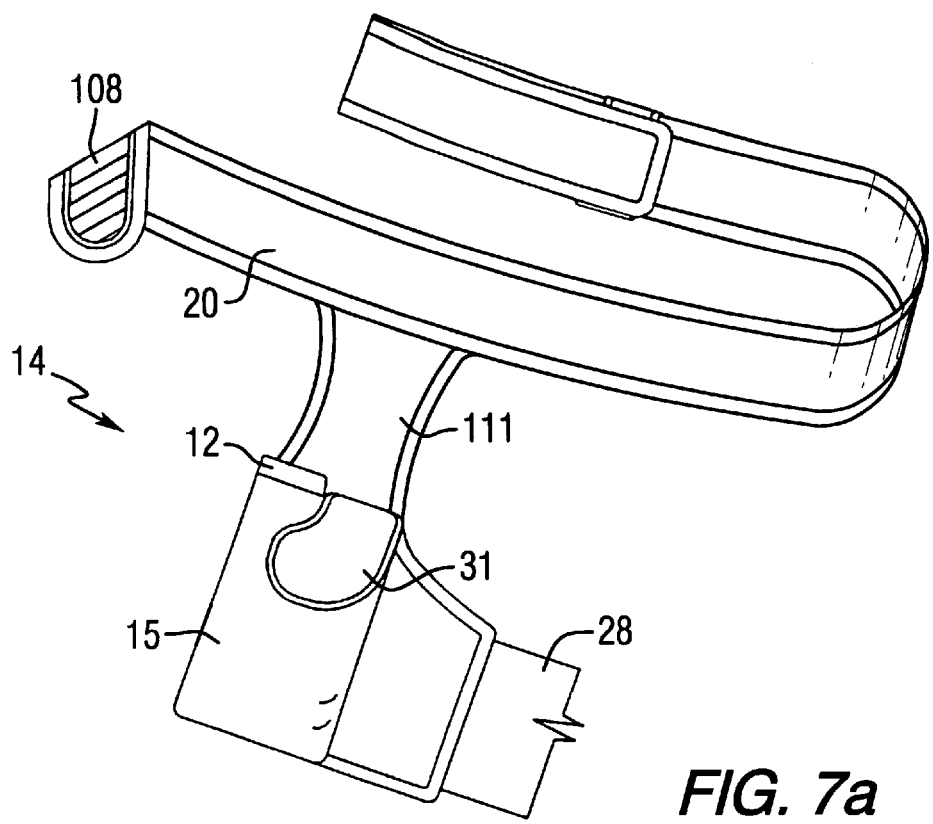
FIG. 7, consisting of FIGS. 7a and 7b, 7c and 7d, is an overall view of a monitor-defibrillator holster and waist belt according to the present invention.
Figure 7B:
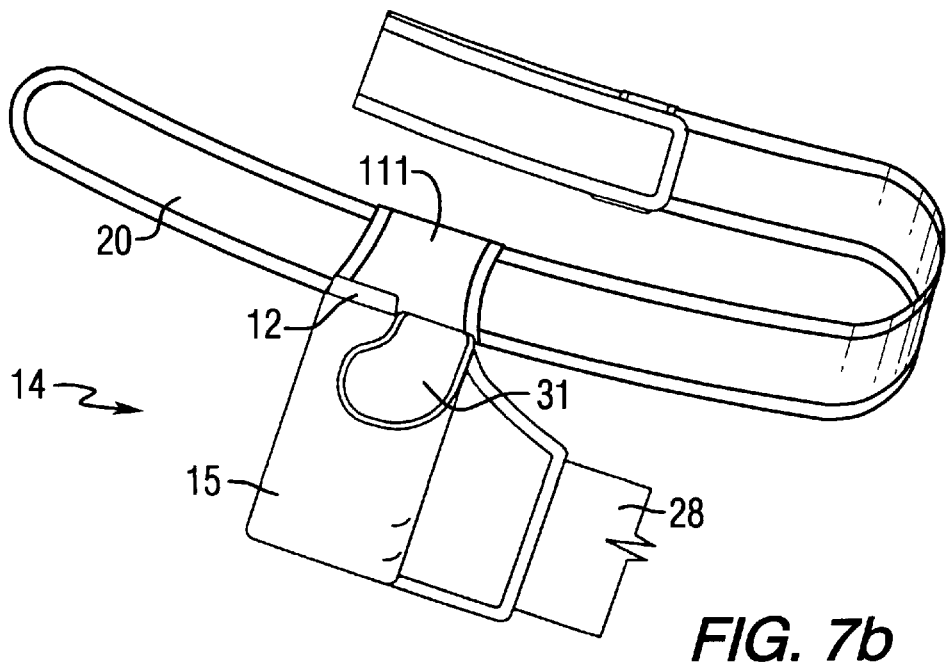
Figure 7C:
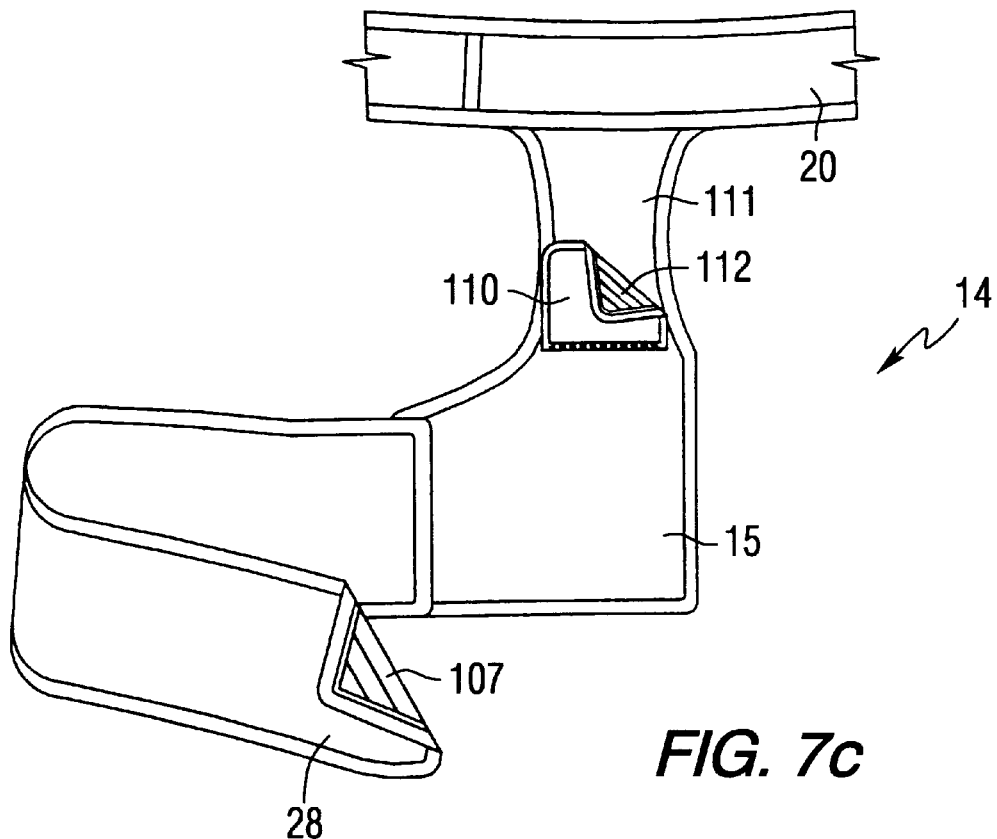
Figure 7D:
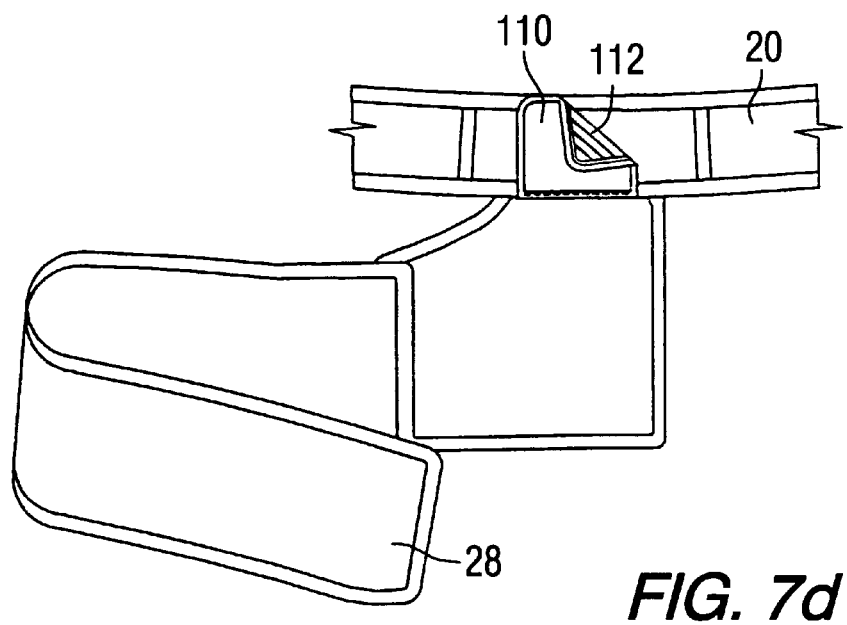
Figure 8:
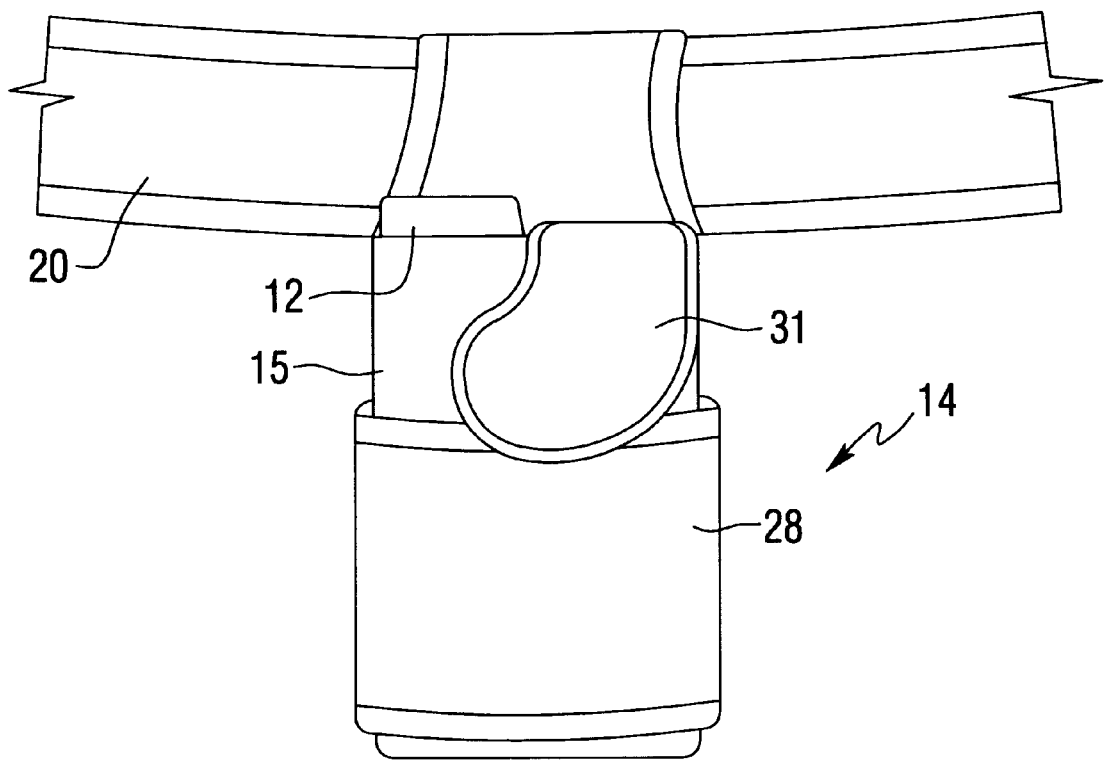
FIG. 8 is a view of the monitor-defibrillator holster with a thigh strap in a stowed position.

Referring to FIGS. 1 and 7a, the design allows the pocket 15 containing the monitor-defibrillator 12 to be worn in a low position, at the left thigh. The pocket 15 may also be worn at the waist, in a high position, over the left hip as in FIG. 7b. Optionally, a thigh strap 28, integral to the monitor-defibrillator holster 14, may be used to restrain the pocket in the low position as in FIG. 1 if desired, while lounging or sleeping. Additionally, the thigh strap 28 may be stowed by wrapping it around the pocket as in FIG. 8, in either the high or low position, as desired by the patient. It is retained in the stowed position by a fabric hook fastener 107. In the low position, the holster waist belt 20 may be rotated at the waist to place the holster pocket 15 either at the outside of the thigh or inside the thigh to permit lying on one's left side. Again, the thigh strap 28 may be utilized or stowed as desired. A fabric hook fastener 108 is provided on the end of the belt to fasten the belt ends at the patient's waist. Additionally, a hook fastened retainer 110 is provided on the back of the monitor-defibrillator pocket 15 to retain the placement of the pocket, relative to the belt 20, in either the low position 7c or the high position 7d. The strap 111 linking the pocket 15 and the belt 20 may be folded over twice to adjust the placement of the pocket 15 in the high position. The retainer 110 with fabric hook 112 attached is then pressed down onto the pile belt material to mate the fastener. In like manner, the strap 111 may be unfolded twice to adjust the placement of the pocket 15 in the low position.

Figure 9:
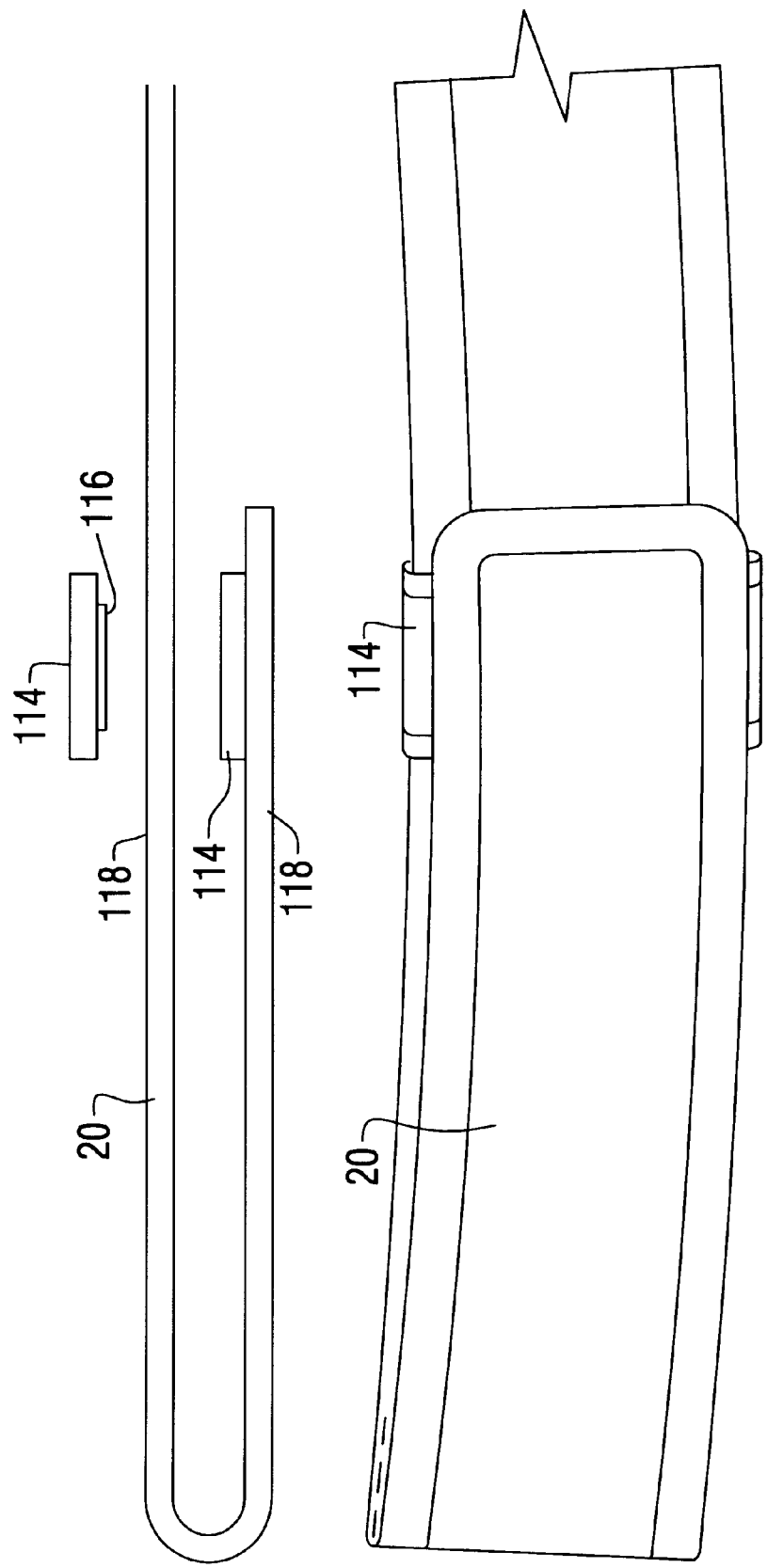
FIG. 9 is a detailed view of a waist belt length-adjustability means.

Turning now to the waist belt 20 length adjustment, per FIG. 9, a loop 114 of trilaminate fabric material is sewn onto the belt end at the patient's right. The inner surface of this loop has attached a piece of fabric hook material 116. This hook material, when pressed onto the pile belt surface 118, locks the belt length at the position chosen. The practical range of adjustment of the belt 20 length, as described, is from twelve (12) inches to fifty-five (55) inches. It should be noted, however, that the smallest circumference obtainable is virtually zero inches, by overlapping the belt sections upon themselves as in a spiral. Additionally, by utilizing an extension, assembled similarly to the end extensions 70 for the above-described chest garment, and fastened by additional fabric hook fasteners, the largest circumference obtainable can be extremely large.

While specific embodiments of the invention have been described in detail, it will be appreciated by those skilled in the art that various modifications and alterations would be developed in light of the overall techniques of the disclosure. Accordingly, the particular arrangements disclosed are meant to be illustrative only and not limiting as to the scope of the invention which is to be given the full breadth of the appended claims and in any and all equivalents thereof.

We claim:

1. A support garment for a patient-worn energy delivery apparatus, the support garment comprising:
    (a) a chest garment having an upper portion and a lower portion, and a first electrode pocket;
    (b) a pair of side portions extending generally laterally from either side of the lower portion, said side portions attachable to each other to define a waist for the chest garment;
    (c) a pair of shoulder straps, each of said shoulder straps attached at one end to the upper portion and at their respective opposite ends to each of said side portions; and
    (d) means for releasably securing a plurality of electrodes to the support garment.

2. The support garment as recited in claim 1, further comprising means for adjusting the waist of the chest garment.

3. The support garment as recited in claim 1, wherein said releasable securing means comprises an inner layer having a plurality of electrode ports, said inner layer including a top section attached to the chest garment and a lower section releasably attached to the chest garment.

4. The support garment as recited in claim 3, wherein said plurality of electrode ports further comprise an elastomeric material for releasably retaining electrodes therein.

5. The support garment as recited in claim 3, wherein said means for releasably securing said plurality of electrodes further comprises an electrode harness disposable between the lower portion of the chest garment and the inner layer, said electrode harness being removably attachable to the inner layer and having length adjusting means.

6. The support garment as recited in claim 1, further comprising means for supporting a monitor-defibrillator, said supporting means including a waist belt, a holster pocket and a strap connecting the holster pocket to the waist belt, wherein the waist belt has an adjustable length.

7. The support garment as recited in claim 6, wherein the waist belt includes an outer layer constructed of a fabric loop material and an end section of the waist belt includes a fabric hook fastener such that the end section is attachable to any portion of the outer layer of the waist belt.

8. The support garment as recited in claim 6, wherein the holster pocket is attachable to the waist belt in one of a high position or a low position.

9. A support garment for a patient-worn energy delivery apparatus, the support garment comprising:
    (a) a chest garment further comprising:
        (i) a back panel having a first electrode pocket;
        (ii) a pair of side portions extending generally laterally from either side of a lower portion of the back panel; and
        (iii) a pair of shoulder straps connected at one end to an upper portion of the back panel and connectable at an opposite end to each of said side portions;
    (b) an inner layer having a top section and a bottom section, the inner layer further comprising:
        (iv) means for removably retaining the bottom section of the inner layer to the lower portion and said side portions;
        (v) means for retaining at least one sensing electrode in said inner layer;
        (vi) a second treatment electrode pocket;
    (c) an electrode harness further comprised of:
        (vii) at least one sensing electrode;
        (viii) a first treatment electrode to be disposed in the first electrode pocket;
        (ix) a second treatment electrode to be disposed in the second electrode pocket; and
    (d) a means for supporting an energy delivery apparatus.

10. The support garment as recited in claim 9, wherein said means for retaining at least one sensing electrode comprises an elastomeric material in said inner layer for releasably retaining electrodes therein.

11. The support garment as recited in claim 9, wherein said electrode harness is disposed between the lower portion of the chest garment and the inner layer, said electrode harness being removably attachable to the inner layer and having length adjusting means.

12. The support garment as recited in claim 9, wherein said means for supporting an energy delivery apparatus further comprises a waist belt, a holster pocket and a strap connecting the holster pocket to the waist belt, wherein the waist belt has an adjustable length.

13. The support garment as recited in claim 12, wherein the waist belt includes an outer layer constructed of a fabric loop material and an end section of the waist belt includes a fabric hook fastener such that the end section is attachable to any portion of the outer layer of the waist belt.

14. The support garment as recited in claim 13, wherein the holster pocket is attachable to the waist belt in one of a high position or a low position.

15. The support garment as recited in claim 12, wherein the holster pocket includes a strap for securing the holster pocket to a thigh of a patient.

\* \* \* \* \*